(12) United States Patent
Laugharn, Jr. et al.

(10) Patent No.: US 9,103,755 B2
(45) Date of Patent: Aug. 11, 2015

(54) SAMPLE HOLDER AND METHOD FOR FRAGMENTING SAMPLE MATERIAL

(71) Applicant: Covaris, Inc., Woburn, MA (US)

(72) Inventors: James A. Laugharn, Jr., Winchester, MA (US); Ion A. Tsinteris, Somerville, MA (US)

(73) Assignee: Covaris, Inc., Woburn, MA (US)

( * ) Notice: Subject to any disclaimer, the term of this patent is extended or adjusted under 35 U.S.C. 154(b) by 381 days.

(21) Appl. No.: 13/681,582

(22) Filed: Nov. 20, 2012

(65) Prior Publication Data

US 2013/0160576 A1 Jun. 27, 2013

Related U.S. Application Data

(60) Provisional application No. 61/562,658, filed on Nov. 22, 2011.

(51) Int. Cl.
*G01N 37/00* (2006.01)
*G01N 1/28* (2006.01)
*G01N 1/42* (2006.01)

(52) U.S. Cl.
CPC ............... *G01N 1/28* (2013.01); *G01N 1/286* (2013.01); *G01N 1/42* (2013.01); *G01N 2001/2866* (2013.01)

(58) Field of Classification Search
CPC .............. G01N 1/00; G01N 1/28; B01L 9/06
USPC ........................................................ 73/864.91
See application file for complete search history.

(56) References Cited

U.S. PATENT DOCUMENTS

| | | | |
|---|---|---|---|
| 4,072,275 A | 2/1978 | Bartels | |
| 4,509,695 A | 4/1985 | Bessman | |
| 5,425,921 A * | 6/1995 | Coakley et al. | 422/547 |
| 8,431,413 B2 * | 4/2013 | Dority et al. | 436/500 |
| 2002/0066812 A1 | 6/2002 | Gazeau | |
| 2003/0066915 A1 | 4/2003 | Taylor | |
| 2007/0099189 A1 | 5/2007 | Gomez | |
| 2009/0317884 A1 | 12/2009 | Laugharn, Jr. | |

FOREIGN PATENT DOCUMENTS

EP 1770158 A2 4/2007

OTHER PUBLICATIONS

International Search Report and Written Opinion mailed Jul. 11, 2013 in connection with PCT/US2012/066043.

* cited by examiner

*Primary Examiner* — Hezron E Williams
*Assistant Examiner* — Rodney T Frank
(74) *Attorney, Agent, or Firm* — Wolf, Greenfield & Sacks, P.C.

(57) ABSTRACT

Method and apparatus for holding and/or treating a sample material. A sample may be positioned in a vessel and a crushing force may be applied to the sample material while in the vessel, e.g., by a plunger that is part of a cap to pulverize the sample at cryogenic temperatures. The sample holder may include an acoustic window arranged to admit acoustic energy into the vessel for acoustic treatment of the sample. A flexible film may be used at a portion of the vessel, e.g., at the acoustic window, to cooperate with a plunger for crushing a sample.

52 Claims, 10 Drawing Sheets

SAMPLE HOLDER AND METHOD FOR FRAGMENTING SAMPLE MATERIAL

CROSS-REFERENCE TO RELATED APPLICATIONS

This application claims the benefit of U.S. Provisional Application No. 61/562,658, filed Nov. 22, 2011, which is hereby incorporated by reference in its entirety.

BACKGROUND

A first step in sample analysis typically involves collecting the sample. For example, a first step in a biological analysis such as RNA gene expression profiling or protein biomarker profiling is to collect a particular sample so that its biochemical constituents can be analyzed. However, prior to such analysis, a solid sample specimen, typically, is prepared by deconstructing it into a plurality of smaller fragments of the specimen to enable more accurate analysis.

A challenge of sample preparation is that the types of samples are diverse. For example, samples may be biological, non-biological or a combination thereof. They may be from animals or plants. Samples may include, without limitation, cells, tissues, organelles, bones, seeds, chemical compounds, minerals, metals, or any other material for which analysis is desired.

Sample preparation is particularly challenging for solid biological samples, such as tissue samples. Physical and/or chemical approaches are often employed to disrupt and homogenize the solid sample for biochemical extraction. While appearing deceptively simple, transitioning a sample of biologically active tissue, for example, on the order of 1 gram, to a plurality of biomolecules that are stabilized and isolated in an appropriate analytical solution is exceedingly complex, very difficult to control, and prone to introduction of errors and/or sample constituent degradation.

Another challenge associated with sample preparation relates to the lability of the target molecules. For some applications, an overriding criterion is to retain the native biochemical environment prior to sample collection and throughout the extraction process, without perturbing the biochemical constituents to be analyzed. For example, RNases are extremely robust and may significantly degrade the mRNA profile of a tissue sample if the RNases are not immediately stabilized (typically thermal or chemical inactivation) at the time of tissue collection and during sample processing or homogenization. Often, to minimize perturbation of the biochemical profile of the sample, the tissue is flash-frozen (e.g., via direct immersion of the sample following procurement in liquid nitrogen) and stored at cryogenic temperatures (e.g., −80 degrees C. or lower), which inhibits degradative processes.

SUMMARY OF INVENTION

Aspects of the invention address at least some of these challenges by providing, in various embodiments, systems, methods and devices for collecting, stabilizing, fragmenting and/or acoustic treatment of samples. As described above, analysis of biological and non-biological sample specimens often begins with collection of a sample of relatively large size. Before the constituents of such a sample can be effectively analyzed, the sample is typically fragmented into a plurality of smaller specimens. Such smaller specimens can then be stored, analyzed, and/or further processed. In one embodiment, a sample holder includes a vessel arranged so that a sample may be placed into the vessel, frozen (e.g., by exposure to liquid nitrogen or other suitable cryogen), and then fragmented, broken, or otherwise crushed without removing the sample from the vessel. In some cases, the vessel may be used for extended storage of the sample in an uncrushed and frozen state (e.g., at temperatures around or below −40 degrees Celsius), followed by subsequent crushing of the sample in the vessel. Thereafter, the sample may be treated with acoustic energy, e.g., to disrupt cell structures or other portions of the sample.

A sample may include any material. Exemplary samples include, but are not limited to, bones, teeth, seeds, plants, pathological or non-pathological animal tissue (e.g., muscle, liver, kidney, lung, brain, pancreas, prostate, ovary, breast, etc.), tumor tissue, rocks, mineral samples, tree bark, and/or food products. Exemplary constituents include, but are not limited to, nucleic acids, amino acids, polypeptides, bacteria, viruses, fungi, spores, small organic molecules, small inorganic molecules, metals, minerals, ores, and the like. The sample may be relatively soft, such as a tissue sample, may be relatively hard, such as a bone or mineral sample, and may include sharp knife-like edges and/or sharp needle-like points. By way of a more particular example of the medical application of the invention, it may be used to process pathological and/or non-pathological tissue samples harvested from a patient. Such samples include, but are not limited to, putative tumor samples taking during a biopsy.

In one aspect of the invention, a sample holder may include a vessel defining an interior space to hold a sample and an opening through which the interior space is accessible. An acoustic window may be arranged as part of the vessel to admit acoustic energy into the interior space for acoustic treatment of a sample by applying focused acoustic energy to the sample. The acoustic energy may be used, for example, for performing any one of: cooling, heating, fluidizing, mixing, stirring, disrupting, increasing permeability of a component of, enhancing a reaction of sterilizing, and/or further fragmenting the sample material. In some embodiments, the sample holder may be arranged for use with an acoustic treatment device, such as that described in U.S. Pat. No. 6,948,843 and/or currently sold by Covaris, Inc. of Woburn, Mass. The sample holder may also include cap that has a cover and a plunger arranged to engage with the vessel so as to cover the opening. The plunger may be arranged for extension into the interior space and movement from a first position to a second position relative to the vessel to crush the sample in the interior space. For example, the plunger may take the form of a rod that extends into the vessel and can be moved to crush a sample between a distal end of the rod and an opposed portion of the vessel, such as the acoustic window. In some embodiments, the vessel may be placed in a device arranged to apply a crushing impact force to the first vessel and first sample material, e.g., as described in U.S. Patent Publication US 2005/0132775 which is hereby incorporated by reference in its entirety.

A sample holder that can be used to store a sample, including storage in cryogenic conditions, fragment or otherwise crush a sample, as well as acoustically treat the sample provides advantages over existing tools. For example, some storage vessels are not intended for use in sample fragmenting, whether in cryogenic conditions or not, or for use in acoustic treatment. Other vessels may be suitable for sample fragmenting, but not for long term storage or acoustic treatment (e.g., because of vessel size, shape or other configuration). Likewise, for vessels suitable for acoustic treatment—some may be suitable for long term storage, but not for sample fragmenting. By providing a vessel capable of holding a sample from sample collection through acoustic treatment, any need to transfer a sample from one vessel to another for different operations can be eliminated, along with risk of sample contamination or other exposure to an external environment.

In another aspect of the invention, a sample holder includes a vessel defining an interior space to hold a sample, and an opening through which the interior space is accessible. A cap may include a cover and a plunger arranged to engage with the vessel so as to cover the opening. The plunger may be arranged to extend into the interior space for movement from a first position to a second position to provide a force to the sample to crush the sample in the interior space. The cover may be arranged to be put in a storage condition in which the plunger is locked in position relative to the vessel to define a specified volume in the interior space, such as a volume of 10 microliters to 1 milliliter. Such an arrangement may be useful, e.g., where the cap or vessel includes a fluid inlet through with a liquid can be added to the interior space. With the cap defining a specified volume in the interior space, liquid, such as a reagent, can be added to the vessel via the fluid inlet to fill the specified volume. Thus, a desired sample volume can be provided in the vessel without measuring the liquid added to the vessel. Also, the sample holder can provide consistent conditions, such as for storage of the sample. The fluid inlet may include a septum arranged to permit both inflow of liquid and outflow of fluid, e.g., a liquid reagent can be added to the interior space via the inlet while air or other gas in the interior space is allowed to escape through the inlet. Alternately, another exit path for displaced gas may be provided.

In another aspect of the invention, a sample holder may include a vessel defining an interior space to hold a sample, a top opening through which the interior space is accessible, a bottom opening, and a flexible film covering the bottom opening. A cap, including a cover and a plunger, may be arranged to engage with the vessel so as to cover the opening and seal the interior space closed. The plunger may be arranged to extend into the interior space for movement from a first position to a second position to urge a sample toward the flexible film and provide a force to the sample to crush the sample in the interior space. A sidewall of the vessel may be made rigid, e.g., to guide the movement of the plunger. In some embodiments, a sample positioned between the flexible film and a distal end of the plunger may be crushed between the flexible film and the plunger, e.g., by way of an impact force applied by the plunger. In some crushing operations, the vessel may be positioned so that the flexible film is arranged over an anvil of a crushing device. The plunger may be arranged under a hammer of the crushing device so that as the hammer is urged toward the anvil, the plunger is driven toward the flexible film and underlying anvil, applying a crushing force to a sample between the flexible film and the anvil.

Providing a sample holder that has a flexible film as one surface against which a sample is crushed can provide enhanced features. For example, the flexible film may function as a kind of liner or barrier layer that allows the anvil (or hammer) of a crushing device to exert the crushing force (including a reaction force) to the sample while the flexible film simply functions to shield the sample from the exterior environment. The flexible nature of the film may allow the film to conform to irregularities of the anvil (or hammer) of a crushing device and/or accommodate misalignment of the sample holder with the anvil (or hammer). For example, a sample holder with a rigid bottom that is not in complete contact with the anvil may experience high stresses upon impact because portions of the vessel bottom are required to provide the crushing force without the support of the underlying anvil. This may cause the sample holder to crack or break, which would not only expose the sample to the external environment, but may also cause the crushing operation to fail.

In another aspect of the invention, a vessel may define an interior space to hold a sample and have an opening at an upper side of the vessel through which the interior space is accessible. A cap having a cover and a plunger may be arranged to engage with the vessel so as to cover the opening and seal the interior space closed. The plunger may be arranged for extension onto the interior space and movement from a first position to a second position relative to the vessel to provide a force to a sample to crush the sample in the interior space. The cap may be arranged to be put in a storage condition, in which the plunger is prevented from movement to the second position, or in a crush-enable condition, in which the plunger is released for sliding movement from the first position to the second position. In this way, the cap could be arranged to lock the plunger and prevent its movement to crush a sample, such as when the vessel is used to store a sample for extended periods of hours, days, weeks, months, etc. Also, since the crush-enable condition allows sliding movement of the plunger, the plunger may be used to apply a rapid, short-duration impulse force to the sample, e.g., suitable to fragment a hard sample and/or a sample that is frozen without generating excessive heat in the sample. This is in contrast to other types of engagements between the plunger and the vessel that do not allow for sliding movement.

The vessel and cap may be arranged in a variety of different ways, and several illustrative embodiments are discussed below, although such embodiments do not provide an exhaustive list. In one arrangement, the cap may be arranged to maintain a hermetic seal for the interior space in both the first and second positions of the plunger. For example, the plunger may have an o-ring or other seal that engages with the vessel and isolates at least a portion of the interior space from an exterior environment, e.g., in a way similar to the way a syringe plunger engages with a syringe barrel. The seal may allow the plunger to move in the interior space, e.g., may allow sufficient amounts of air or other fluid to leak by the seal as needed for plunger movement into or out of the interior space, but will otherwise maintain a hermetic seal. Alternately, the seal between the plunger and the vessel may be broken, e.g., by the vessel size increasing in size near a lower end so that a seal element on the plunger disengages with the vessel. This may permit the plunger into the interior space without compressing gas in the interior space, and allow the plunger to provide a more consistent and predictable force to the sample.

As mentioned above, the vessel may have an acoustic window that includes an opening in the vessel which is covered by a film or other suitable element. The acoustic window may allow acoustic energy to relatively freely pass into the interior space, e.g., to form an acoustic focal zone suitable to induce cavitation, mixing, or other movement in the sample. If a film is used to form an acoustic window, the film may have a thickness of between about 0.5 mil and 5 mil, and may be made of a polyimide, a polysulfone, a fluorinated polymer or a liquid crystal polymer material. The acoustic window may be arranged to cooperate with the plunger to provide a force to a sample to crush the sample, e.g., the acoustic window and the plunger may be arranged to provide a force to a sample located between the acoustic window and the plunger. In addition, the acoustic window may function to transfer heat between the sample and an exterior environment, such as a water bath or other acoustic coupling medium in which at least a part of the holder is immersed. For example, heat generated in the sample by acoustic treatment may be released by conduction and/or radiation through the acoustic window. If used, a relatively thin film window may transfer heat much more rapidly than other portions of the vessel, helping to keep the sample at a desired temperature. In some cases, maintaining a sample at a constant temperature during acoustic treatment can be important, and an acoustic window may help maintain isothermal conditions in the sample.

Whether an acoustic window or flexible film is used or not, the holder may be arranged to provide a crushing force to a sample material that transfers energy to the sample of at least about 10 Joules or more. Relatively high crushing forces and/or energies may be applied to a sample at a wide range of temperatures, including temperatures below about −40 degrees Celsius. For example, the sample holder and sample may be immersed in liquid nitrogen to cool the sample, and subsequently inserted into a crushing device which drives the plunger to crush the sample.

The cap may be arranged to engage with the vessel in a storage position in which the plunger is located at a first depth in the interior space, and in a crush position in which the plunger is located at a second depth in the interior space that is greater that the first depth. In some embodiments, the cover and the plunger may be fixed relative to each other, and may be driven toward the vessel to insert the plunger further into the vessel and crush a sample. In some arrangements, with the plunger at the second depth, rotation of the cap relative to the vessel may withdraw the plunger at least partially from the interior space. For example, while the plunger may be permitted to slide relative to the vessel to crush the sample, rotation of the plunger and/or cover may withdraw the plunger at least partially from the vessel. This arrangement may be useful, for example, when a seal is present between the plunger and the vessel such that a vacuum or otherwise low pressure condition is produced when an attempt is made to withdraw the plunger from the vessel. By having the plunger withdraw by rotation of the plunger and/or cover, a mechanical advantage may be provided (e.g., like that of a screw thread) to help withdraw the plunger from the vessel.

In some embodiments, the plunger may be prevented from movement into the interior space with the cap in the storage condition. This may help prevent inadvertent movement of the plunger into the vessel, such as during storage. The cap may also be moveable into a crush-enabled condition in which the plunger is movable to crush a sample in the interior space. Thus, the cap may be moved (e.g., rotated) from the storage condition to the crush-enabled condition when a user wishes to crush the sample.

The sample holder may be arranged for use with a variety of analysis tools, such as microscopes and other imaging devices, impact devices, acoustic treatment devices, and so on. Accordingly, the sample holder may allow a variety of processes and treatments to be performed on the sample, such as freezing, crushing and acoustic treatment, as well as analysis processes such as visual and other inspections, all without removing the sample from the holder.

These and other aspects of the invention will be apparent from the following description and claims.

BRIEF DESCRIPTION OF THE DRAWINGS

Aspects of the invention are described with reference to illustrative embodiments shown in the drawings, in which like numerals reference like elements, and wherein.

DETAILED DESCRIPTION

It should be understood that illustrative embodiments are described in accordance with aspects of the invention. However, the embodiments described are not necessarily intended to show or incorporate all aspects of the invention, but rather are used to describe a few illustrative embodiments. Thus, aspects discussed herein are not intended to be construed narrowly in view of the illustrative embodiments. In addition, it should be understood that aspects of the invention described may be used alone or in any suitable combination with other aspects also described.

Figure 1:
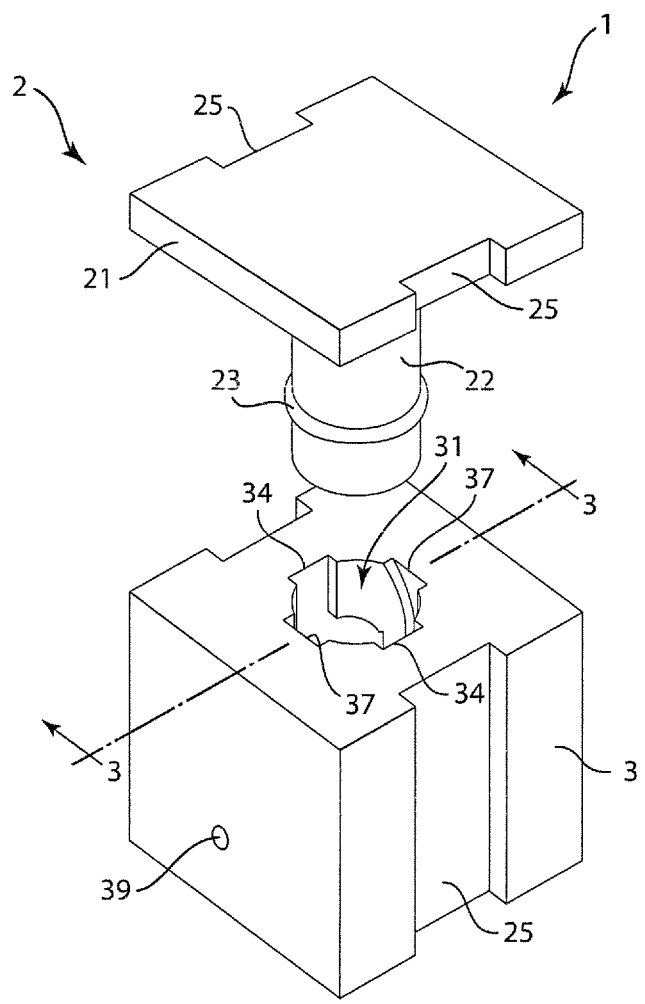
FIG. 1 shows a top perspective view of a sample holder in an illustrative embodiment.
Figure 2:
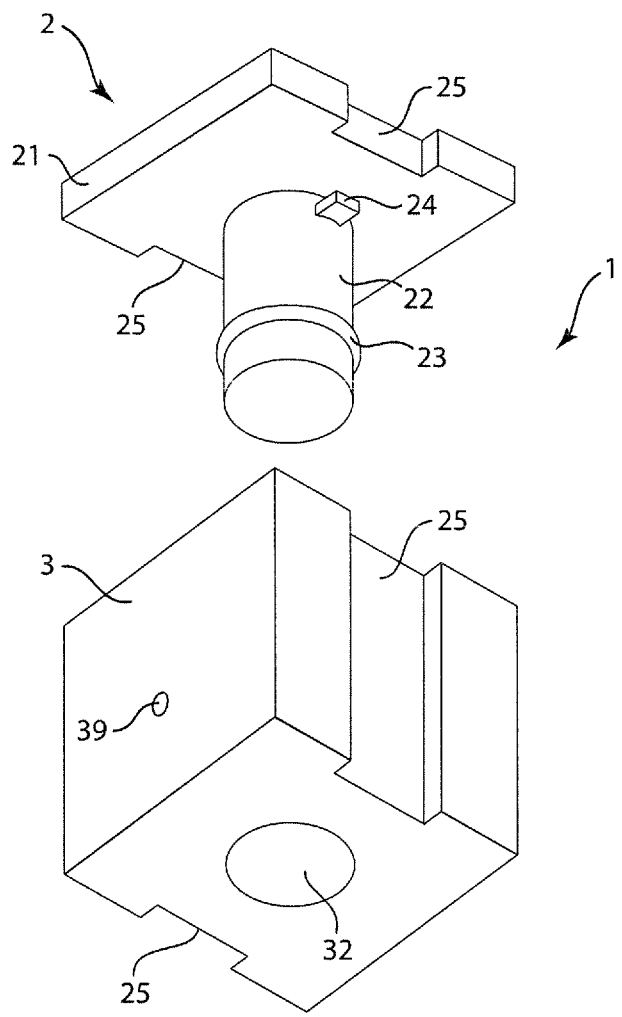
FIG. 2 shows a bottom perspective view of the sample holder of FIG. 1.

FIGS. 1 and 2 show top and bottom perspective views of an illustrative embodiment of a sample holder 1 that incorporates one or more aspects of the invention. In this embodiment, the sample holder 1 includes a vessel that is made of a polymer material (such as polycarbonate, polyethylene, polypropylene, polyimide, PTFE, etc.), has an overall cube shape, and is arranged to hold a 5 to 50 mg tissue sample. However, it should be understood that the vessel 3 may have any size, shape or other configuration, may be arranged for use with a wide variety of different samples, and may be made of any suitable material or combination of materials, including glass, metal, composites, etc. Also, while the sample holder 1 includes one vessel 3, the holder 1 may include two or more vessels. The holder 1 in this embodiment is arranged to hold a sample material for crushing (discussed in more detail below) and acoustic treatment of the sample, but other embodiments may be arranged only for crushing, or only for acoustic treatment, or only for other processes. The holder 1 may also be used to store a sample for any suitable length of time and in a variety of different conditions based on the particular sample, its intended use, etc. Exemplary storage periods include short term storage for minutes (e.g., less than or equal to 30 minutes) or hours (e.g., less than or equal to 1 to 12 hours). Further exemplary storage periods include overnight storage or storage for 1 or more days, weeks, months, or years.

In accordance with an aspect of the invention, the vessel 3 may include an acoustic window 32 that is arranged to allow acoustic energy to relatively freely pass into the interior space 31 of the vessel 3 for acoustic treatment of a sample. As a result, a majority of the vessel 3 need not necessarily be made of a material or construction suitable for transmission of acoustic energy into the interior space from an exterior source, but rather may be made without concern for acoustic transmittance. This may allow the vessel to be made more inexpensively (as constructions that are less acoustically transparent may be made of less expensive material and/or using less expensive processes or designs) and/or to allow the vessel to function for other purposes, such as crushing a sample. Thus, a sidewall of the vessel may be made relatively robustly to withstand pressures and other forces that the vessel may need to withstand without support, while still allowing the vessel to be used with acoustic treatment of the sample. The acoustic window 32 may be made of a thinner and/or less robust material, yet still withstand crushing forces, at least in part, because the window 32 may be supported by an anvil or other part of a crushing device, as discussed more below. While in this embodiment the acoustic window 32 is generally flat with a circular shape, other arrangements are possible. For example, the window 32 may be convex, concave, hemispherical, or, in short, take any suitable size, shape or other configuration. Also, in this embodiment, the window 32 is located at a bottom of the vessel 3, but may be positioned elsewhere, such as at a sidewall of the vessel, whether extending entirely around the vessel sidewall or only located at a portion of the sidewall. In other embodiments, the acoustic window 32 may define the entire lower portion of the vessel 3, e.g., in the form of a flat plate or hemispherical shell element that is attached to a sidewall portion of the vessel.

In one embodiment, the vessel may include a flexible film that covers a bottom opening of the vessel. As discussed above, using a flexible film in this way may allow the film to function as an acoustic window and/or as a liner that allows the anvil (or hammer) of a crushing device to bear the crushing force, and thus relieve the vessel, at least in part, from withstanding those forces. For example, a sample holder with a rigid bottom that is not in complete contact with the anvil of a crushing device may experience high stresses upon impact that cause the sample holder to crack or break. Also, a flexible film may be relatively thin and made generally acoustically transparent, thus allowing the flexible film to function as an acoustic window 32. As a result, the flexible film may allow the vessel to function as a sample holder for use in acoustic treatment of a sample in addition to, or in lieu of, as for crushing a sample. The film may have a thickness of between about 0.5 mil and 5 mil, and may be made of a polyimide, a polysulfone, a fluorinated polymer or a liquid crystal polymer material. In this embodiment, the film may be a 3-4 mil piece of Kapton® made by the DuPont Corp having a diameter of about 20 mm, but other sizes and shapes may be used. The film, as with any component used to make an acoustic window 32, may be co-molded with other portions of the vessel 3, may be adhered, welded, clamped or otherwise attached to other portions of the vessel, may be made as a single, unitary piece with other portions of the vessel, etc.

In some cases, the arrangement for a flexible film may depend at least in part on the mechanical properties of the sample 10 (e.g., whether the sample is relatively hard, relatively soft, forms sharp or pointed shards when fragmented, etc.) and the temperature at which fragmentation is to occur. For example, a brain sample may require a particular film layer thickness (e.g., 1 mil layer of Kapton). Alternatively, a bone, seed, or rock sample, which may have sharp and or pointed features, may require a thicker film layer thickness (e.g., 4 mil layer of Kapton). Also, an additional reinforcement layer, for example, of a non-woven polymer material, such as Tyvek™ (available from Dupont), reinforcement by woven or non-woven material, or other suitable reinforcement may be provided for the film.

In accordance with an aspect of the invention, the holder 1 includes a cap 2 that includes a plunger 22 arranged to extend into the interior space 31 of the vessel 3 and apply a crushing force to a sample in the vessel 3. The plunger 22 may cooperate with an acoustic window 32 (e.g., a flexible film) that is located at a bottom of the vessel 3 in crushing the sample (e.g., by squeezing the sample between a distal end of the plunger 22 and the window/film 32), or may work with another portion of the vessel if a window/film 32 is not provided or is not positioned to cooperate with the plunger 22. For example, in some embodiments, a window/film 32 may be located on a sidewall of the vessel 3 and the plunger 22 may work with the bottom portion of the vessel to crush a sample. In this embodiment, the cap 2 also includes a cover 21 from which the plunger 22 depends, but other arrangements are possible. For example, the cover 21 could have a through hole through which the plunger 22 can be moved to extend into the interior space 31. Also, in this embodiment, the cover 21 has a square size and shape that is similar to the size and shape of a top end of the vessel 3, but other configurations are possible. For example, the cover 21 could be relatively small and function as a handle for the plunger 22, e.g., provide T-handle, finger loop or tab that could be gripped to manipulate the plunger 22. Thus, the cover 21 need not cover all or even a part of the vessel 3, but instead may cover or otherwise be arranged at a top portion of the plunger 22.

In this embodiment, the plunger 22 and cover 21 are arranged so that the plunger 22 can be fully inserted into the interior space 31 (e.g., so a distal end of the plunger 22 is in contact with, or close to, an acoustic window 32 or other portion at a bottom end of the vessel 3) to exert a crushing force on a sample when a bottom surface of the cover 21 contacts the vessel 3. Of course, other arrangements are possible, such as the plunger 22 "bottoming out" in the interior space 31 without the cover 21 contacting the vessel 3. However, by having the cover 21 function as a stop of plunger movement, the plunger 22 may be prevented from applying too much crushing force and/or damaging the vessel 3.

In accordance with another aspect of the invention, the cap 2 may be arranged so that the plunger 22 can be put in a storage condition in which the plunger is prevented from further moving into the interior space 31, and in a crush-enable condition in which the plunger 22 is movable to crush a sample. In this embodiment, and as will be explained in more detail below, the plunger 22 includes one or more protrusions 24 that interact with surface features of the vessel 3 to prevent and/or allow movement of the plunger 22 in the interior space 31. For example, the protrusions 24 may engage with slot features in the sidewall of the interior space 31 so that in one rotary position, the plunger is locked in place, and in another rotary position, the plunger is free for sliding motion into the interior space 31. In one embodiment, with the plunger locked in place relative to the vessel, the plunger 22 may define a specified volume in the interior space, such as a volume of between about 10 microliters to about 1 milliliter. The vessel 3 may include a fluid inlet 39, e.g., a port that allows liquid to be added to the interior space

31. With the cap 2 defining a specified volume in the interior space 31, liquid (such as a reagent) may be added to the interior space 31 to fill the specified volume. This may allow the vessel 3 to be filled with an accurate volume of material without measuring, e.g., injection of fluid by syringe at the inlet 39 may be continued until fluid exits the inlet 39, indicating that the specified volume has been filled. While the inlet 39 in this embodiment is in the vessel sidewall, other arrangements are possible, such as an inlet 39 arranged in the cap 2, the window 32, etc. The inlet 39 may include a split septum (e.g., a layer of resilient material with a cut to allow insertion and sealing with a syringe tip), a one-way valve, a removable cap or plug, etc.

In another aspect of the invention, the cap may be arranged so that rotary motion of the cap causes at least partial withdrawal of the plunger from the vessel. For example, the protrusions 24 may engage with thread-like surface features in the interior space 31 of the vessel 3 so that when the cap 2 is rotated with the plunger fully inserted into the interior space 31, the thread-like surfaces will engage with the protrusions 24 so as to withdraw the plunger from the interior space 31. This feature may be useful, for example, when a vacuum or other low pressure condition is experienced in the interior space 31 when an attempt is made to withdraw the plunger 22. Such a vacuum or other low pressure condition may be created when the plunger 22 forms a seal with the vessel that restricts air or other fluid from entering the interior space 31 when the plunger is extracted. Such a seal may be created by close contact between a portion of the plunger 22 (such as an o-ring or other seal element 23) and the sidewall of the interior space 31.

In accordance with another aspect of the invention, the cap 2 and/or vessel 3 may include one or more indicators 25 to indicate a condition of the cap 2, e.g., whether the cap is in a storage condition or a crush-enable condition or other. In this embodiment, the cap 2 and the vessel 3 include markings and/or surface features 25 in portions of the cap 2 and vessel 3 that, when aligned, indicate that the cap is in a crush-enable condition. In this condition, the plunger is free for movement into/out of the interior space for crushing the sample. When the indicators 25 are not aligned, the cap 2 is indicated to be in a storage condition in this embodiment. Other indicator arrangements are possible for indicating a cap condition, such as paint or other markings, a strip that extends between the cap and vessel that can be broken or torn when the cap is moved from a storage to crush-enable condition (e.g., like that used with some bottle and cap arrangements to indicate when a cap has been removed from the bottle), a marking and window feature, such as one that includes a window in the cover 21 that allows viewing of a top surface of the vessel 3, and others. For example, the vessel 3 may have markings in the top surface that can be viewed through a window in the cover 21 to indicate the cap condition, e.g., a "C" for crush-enabled and an "S" for storage, or a green spot for crush and a red spot for storage, etc. Also, the vessel and cap may include physical features that not only indicate a cap condition, but physically define the storage and crush-enabled conditions. For example, the cover 21 may include one or more openings and the top surface of the vessel 3 may include one or more posts that extend upwardly from the top surface. The tops of the posts may be viewed through, and received into, the openings with the cap in the crush-enabled condition, allowing the plunger to move into the interior space 31, while with the cap in the storage condition, the openings may be offset from the posts so that the posts are not observable through the windows but instead contact the cover 21 and prevent movement of the plunger into the interior space 31.

Figure 3:
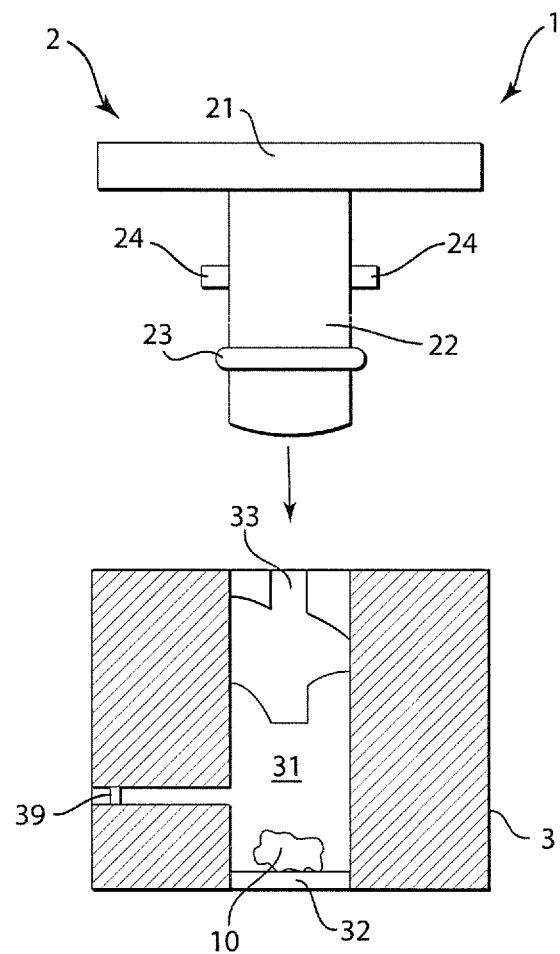
FIG. 3 shows a cross sectional view of the FIG. 1 embodiment while a crushing force is applied to the sample material in the vessel.
Figure 4:
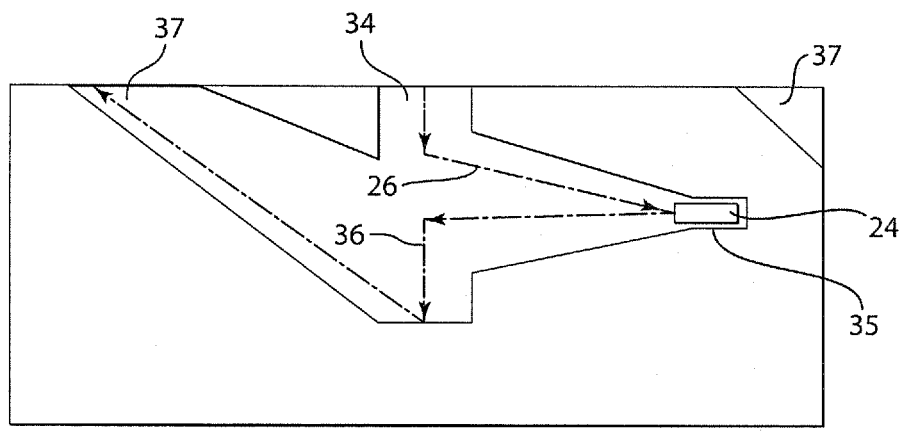
FIG. 4 shows a map of surface features of the internal sidewall of the FIG. 1 vessel.

FIG. 3 shows a cross-sectional view of the sample holder 1 along the line 3-3 in FIG. 1. In this embodiment, the vessel 3 defines the interior space 31 as a generally cylindrical shape into which the plunger 22 can extend. This view also depicts a sample 10 located in the interior space 31 and adjacent the acoustic window/film 32. In this arrangement, the sample 10 may be crushed between a distal end of the plunger 22 and the window/film 32. Surface features 33 formed on the sidewall of the interior space 31 can also be seen which interact with the protrusions 24 of the cap 2 and help control the movement of the plunger 22 in the interior space 31. While the surface features 33 could be arranged in any suitable way, one possible configuration is shown in two-dimensional form in FIG. 4. That is, while the surface features 33 are formed in the cylindrical sidewall of the interior space 31 of the vessel 3 in this embodiment, FIG. 4 shows a portion of the surface features 33 in a flat, two-dimensional form, e.g., in a way similar to how a map of Earth shows Earth's surface features in a flat form. The view of FIG. 4 shows only one half of the surface features that are located on the interior sidewall, i.e., those surface features 33 that are arranged on the half of the sidewall on one side of the line 3-3 in FIG. 1, because the two halves of the interior sidewall are mirror images of each other.

FIG. 4 also shows a path 26 that is followed by a protrusion 24 of the plunger 22 in the various phases of movement of the cap 2 relative to the vessel 3. When the cap 2 is first associated with the vessel 3 so that the plunger 22 is introduced into the interior space, the protrusions 24 are aligned with a respective entrance slot 34 (see FIG. 1) so that the protrusions 24 can pass at least partially into a crush slot 36. With the protrusions 24 introduced into the entrance slots 34, the cap 2 can be rotated clockwise (e.g., 90 degrees) relative to the vessel 3 so that the protrusions 24 move into a storage slot 35. Angled upper and lower surfaces of the storage slot 35 help guide the protrusion 24 to a terminal end of the storage slot 35 (as shown in FIG. 4). When the protrusions 24 reach the terminal end of the respective storage slot 35, further clockwise rotation of the cap 2 is prevented. Moreover, movement of the plunger 2 into/out of the interior space 31 is prevented by capture of the protrusions in the storage slot 35. Also, the seal element 23 on the plunger 22 may engage with the interior sidewall to create a suitable seal for the portion of the interior space 31 in which a sample 10 is located. In this state, the cap 2 is in a storage condition, e.g., a condition suitable for storage of a sample in the vessel for any length of time, although the presence of a seal is not necessarily required. In this embodiment, the indicators 25 on the cap 2 and vessel 3 are not aligned, indicating that the cap is in the storage condition, although such condition may be indicated in other ways.

To place the cap 2 in a crush-enable condition, the cap 2 may be rotated counterclockwise 90 degrees relative to the vessel 3 so that the protrusions 24 move into the crush slots 36. In this state, the indicators 25 are aligned with each other to indicate the crush-enable condition. The crush slots 36 are arranged to allow the plunger 22 to move into the interior space 31 to apply a crushing force to the sample 10. The crush slots 36 may have stop surfaces at a lower end, e.g., to engage the protrusions 24 and help prevent movement of the plunger 22 into the interior space 31 beyond a certain point. Alternately, or in addition, the arrangement of the cover 21 may function as a stop, e.g., by having the cover 21 contact a top surface of the vessel 3 when the plunger 22 is inserted a desired distance into the interior space 31.

While the plunger 22 may be withdrawn from the interior space 31 by pulling on the cover 21 relative to the vessel 3, in this embodiment the surface features 33 include an exit slot 37 that has an angled surface on which a corresponding protrusion 24 can ride as the cap 2 is rotated from the crush-enabled condition. That is, if the cap 2 is rotated counterclockwise (e.g., about 90 degrees) relative to the vessel 3 when the plunger is fully inserted into the interior space, the protrusions 24 may engage with a corresponding exit slot 37 ramp surface so that rotation of the cap 2 withdraws the plunger 22 from the interior space 31. This feature may help withdraw the plunger 22 from the interior space 31 when a vacuum or other low pressure condition is created by an attempt to pull the plunger from the interior space. That is, while the seal element 23 or other arrangement may create a seal to help isolate a portion of the interior space from an exterior environment, the seal may allow at least some air or other fluid to enter into the interior space while the plunger 22 is withdrawn while otherwise maintaining a hermetic seal. Alternately, the seal between the plunger and vessel may be broken during movement of the plunger into the vessel, e.g., by the sidewall widening near the bottom of the vessel. At a desired point, such as when the protrusions 24 reach an upper end of the exit slot 37, the seal element 34 may pass a lower end of the crush slot 36, which may break a seal of the interior space and allow the plunger to be withdrawn more easily.

While in this embodiment, the protrusions 24 are located on the plunger 22, other arrangements are possible. For example, the cover 21 and vessel 3 may include ramped surfaces, protrusions or other elements that interact with the vessel to place the holder 1 in a storage condition, crush-enable condition, and/or to aid in withdrawing the plunger from the interior space. Alternately, the cover 21 and plunger 22 may interact to provide the storage condition, crush-enable condition, and/or to aid in withdrawal of the plunger. For example, the cover 21 may have an opening that includes surface features like that in FIG. 4, and the plunger may include protrusions or other elements that interact with the surface features of the cover to place the cap in the storage condition and/or the crush-enabled condition, as well as assist in withdrawal of the plunger, e.g., after the plunger is fully inserted into the interior space. In other embodiments, a separable portion of the cap 2 may define the storage condition or crush-enable condition. For example, in an embodiment similar to that of FIGS. 1 and 2 but lacking protrusions 24 and surface features 33, a spacer element (e.g., in the form of washer or "U" shaped element) may be arranged to be positioned between the cover 21 and the vessel 3 to prevent plunger movement into the interior space and define the storage condition. Removal of the spacer element may define the crush-enabled condition. For withdrawal of the plunger, the spacer element may include a wedge portion that is inserted into a gap between the cover and vessel and can be pushed into full engagement so as to separate the cover 21 from the vessel 3 and withdraw the plunger 22. In another embodiment, the cover 21 may include a lever-operated cam that is arranged to move to allow full insertion of the plunger, and to be operated to withdraw the plunger from the interior space. Other arrangements are possible for aiding in the withdrawal of the plunger from the interior space.

Figure 5:
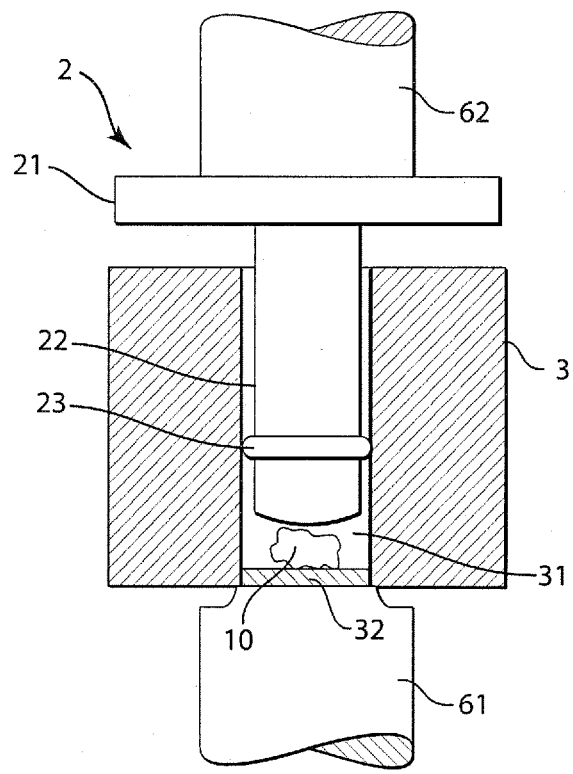
FIG. 5 shows a cross sectional view of the FIG. 1 embodiment with the sample holder associated with a crushing device.
Figure 6:
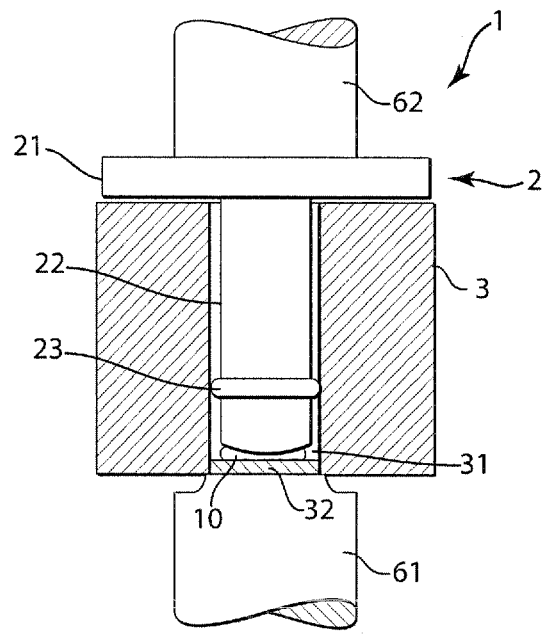
FIG. 6 shows a cross sectional view of the FIG. 1 embodiment while a crushing force is applied to the sample material in the vessel.

FIGS. 5 and 6 show a cross-sectional view of the sample holder 1 of FIGS. 1 and 2 when used to crush a sample. In FIG. 5, the sample holder 1 is arranged so that the vessel 3 is positioned over an anvil 61 of a crushing device, such as one that includes a solenoid-operated hammer 62. In various embodiments, the sample holder 1 may be sized and shaped for insertion into, and functional interoperation with, a mechanical impact device, such as that described in U.S. Patent Publication US 2005/0132775. For example, the anvil 61 and hammer 62 may include metal members that are driven together by a hand-held hammer, an electromagnetically-driven solenoid piston, a pneumatically-actuated device, a hydraulically-actuated device, a gravity actuated device, or any other suitable mechanism. Also, the anvil 61 may remain stationary while the hammer 62 moves toward the anvil 61, or both elements may move toward each other, e.g., as is the case with some vise configurations. Although the crushing device may operate at cryogenic temperatures, the crushing device may also operate at or about room temperature while still applying a crushing force when the sample 10 is at cryogenic temperatures. That is, even though the crushing device may be at room temperature, the crushing device may operate quickly enough so that the transient exposure of the sample holder 1 to the anvil 61 and hammer 62 does not substantially warm the sample 10. This is also the case where the sample 10, itself, is maintained at room or near room temperature. Alternately, the crushing device may operate more slowly to drive the plunger 22 into the vessel 3 or otherwise cause a crushing force to be provided to the sample.

In various embodiments, the crushing device may provide elements for heating or cooling the sample prior or subsequent to fragmenting it. For example, one or both of the anvil 61 and hammer 62 may be chilled (e.g., by liquid nitrogen), and contact of the sample holder 1 with one or both of the elements may chill the sample 10. The mechanical impact from the crushing device may provide a force sufficient to disrupt the macro-structure of the sample 10, and fragment it into a plurality of pieces in the vessel 3. Illustratively, the impact force may be between about 1 Joule and about 25 Joules, and may be applied at temperatures below about −20 degrees C. to about −80 degrees C. or less (such as about −196 degrees C.). Of course, in some embodiments, the sample holder 1 may be arranged for use only at non-cryogenic temperatures, such as room temperature and/or temperatures above the freezing point of water. The impact elements (e.g., anvil and hammer) may impact the vessel 3 one or more times to achieve the desired sample fragmentation. For example, the vessel 3 and sample material 10 may be contacted 1 to 5, or more times, and each impact may have the same or different force or impact energy applied. For example, the impact force may be initially larger to break a large sample into fragments, and then be reduced.

Prior to placing the holder 1 in association with the crushing device, the cap 2 and vessel 3 may be arranged from a storage condition to a crush-enable condition, e.g., by rotating the cap 2 relative to the vessel 3 so as to align indicators 25. The acoustic window/flexible film 32 may be positioned over a portion of the anvil 61 or other impact element so that the window/film 32 is supported by the anvil 62. As noted above, a flexible film 32 may allow the holder 1 to be somewhat misaligned with respect to the anvil 62 during crushing without causing damage to the vessel 3 or compromising an isolated environment for the sample. The cap 2 may be located under the hammer 62 so that when the hammer 62 is driven toward the anvil 61, the plunger 22 is forced into the interior space 31 to crush the sample 10 between the distal end of the plunger 22 and the window/film 32 as shown in FIG. 6. Such crushing may occur at cryogenic or other suitably low temperatures, e.g., after immersing the sample 10 and/or the holder 1 in liquid nitrogen. Although in this embodiment the crushing operation is shown with the plunger moving downward into the interior space, other configurations are possible, such as the plunger moving upward into the interior space, or horizontally into the interior space. Thus, references to top, bottom, downward, etc. are used for ease of reference and do not necessarily limit the way in which a sample holder 1 may be used or configured. After crushing, and if the sample holder 1 is suitably equipped, the plunger 22 may be at least partially withdrawn from the interior space 31, e.g., by rotating the cap 2 relative to the vessel 3. This action may break a seal between the plunger and the vessel, and allow the easier withdrawal of the plunger.

If a flexible film 32 is provided, the film may deflect or otherwise move with application of the crushing force depending on the application, and in some cases the film may deflect up to 1 mm or more. Of course, those of skill in the art will appreciate that the film may deflect to greater extents, such as up to 10 mm or more. In some cases, the deflection of the film 32 may depend on the sample type and/or mass (or volume), e.g., the sample may have a mass or 50 to 250 milligrams or more (or less).

In some embodiments, the window or film 32 may be arranged to deform nondestructively or otherwise withstand the application of the crushing force (e.g., without experiencing cracking, tearing, ripping or other degradation in structural integrity), sufficient to fragment the sample 10 contained within the vessel 3. According to one feature, subsequent to the mechanical impact, the sample holder 1 may maintain sufficient structural integrity to continue to separate the sample material 1 from the external environment. For example, the vessel may maintain the sample in sterile isolation from the external environment.

Embodiments in accordance with the invention may be arranged to accommodate an increase in air or other gas pressure in the vessel 3 during crushing of the sample material 10. That is, when the sample material 10 is impacted in some embodiments, the volume of the interior space 31 in which the sample 10 is held may be decreased, if only momentarily, increasing the gas pressure in the vessel 3. To compensate, and while maintaining a sealed environment for the sample material, the vessel 3 and/or plunger 22 may be arranged to "burp", i.e., to release gas through a one-way valve, through a seal element 23 between the plunger 22 and vessel 3 or other pathway when the sample is impacted. While gas may be released from the vessel 3, the sample holder 1 may be arranged to prevent the inflow of gas into the vessel 3, thus maintaining the sample material isolated from an external environment. In other embodiments, a flexible film 32 and/or other portions of the sample holder 1 may be arranged to accommodate an increase in gas pressure. For example, a portion of the film 32 that is not contacted by the crushing device (if the film 32 is so positioned) may move to accommodate gas in the vessel 3 so as to maintain the same pressure or another elevated pressure that does not compromise a seal of the vessel 3. In one embodiment, a flexible film 32 may include a convex portion that moves (e.g., from a convex configuration to a concave configuration) to accommodate an increase in gas pressure. Other arrangements are possible, such as a gas reservoir, a pressure release valve, expansion chamber, etc., formed as part of the vessel 3 and/or cap 2.

Figure 7:
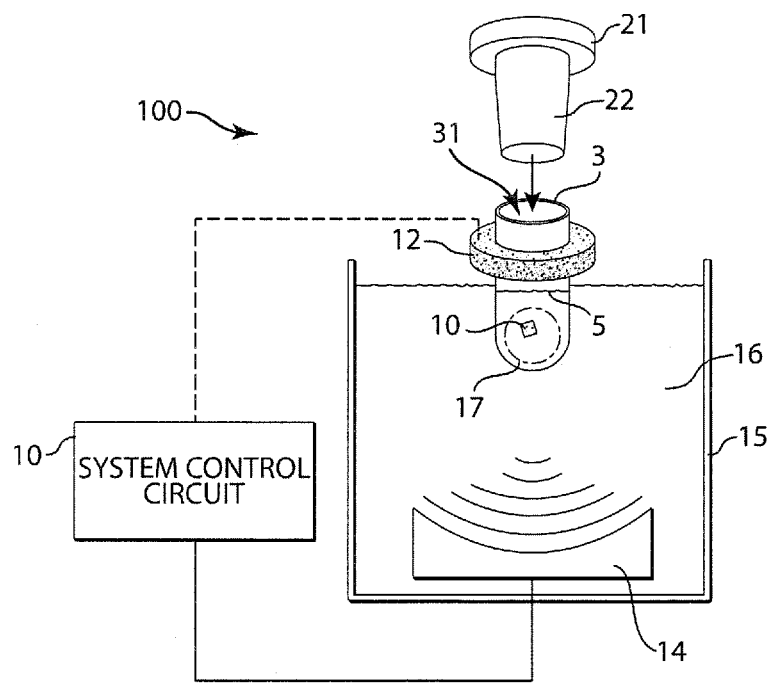
FIG. 7 shows a schematic diagram of an acoustic treatment system using a sample holder in accordance with an illustrative embodiment.

As noted above, the sample holder 1 may be used for acoustic treatment of the sample 10 whether before and/or after crushing of the sample. For example, the sample holder 1 may be arranged for use with an acoustic treatment device, such as that described in U.S. Pat. No. 6,948,843. Thus, the sample holder 1 may be used to provide focused acoustic energy to the sample contained within the vessel for performing any one of: cooling; heating; fluidizing; mixing; stirring; disrupting, increasing permeability of a component of, enhancing a reaction of, sterilizing; and/or further fragmenting the sample material. FIG. 7 shows a schematic block diagram of an acoustic treatment system 100 that may be used with a sample holder 1 to treat a sample with acoustic energy. In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 3. The acoustic transducer 14 may produce acoustic energy within a frequency range of between about 100 kilohertz and about 100 megahertz such that the focal zone 17 may have a width of about 2 centimeters or less. The focal zone 17 of the acoustic energy may be any suitable shape, such as spherical, ellipsoidal, rod-shaped, or column-shaped, for example, and be positioned at the sample 1, e.g., entirely within the interior space 31 of the vessel. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control.

The acoustic treatment system 100 may also include a coupling medium container 15 that is capable of holding a medium 16 (such as water or other liquid, gas, gel, solid, semi-solid, and/or a combination of such components) which transmits acoustic energy from the transducer 14 to the vessel 4. In embodiments where the medium 16 includes a solid or semi-solid, a container 15 need not be provided or a portion of the medium 16 itself may function as a container 15, e.g., to hold a liquid or gas portion of the medium 16. For example, in one embodiment, the transducer 14 may be attached to a solid coupling medium 16 (such as a silica material), which is also attached to a vessel holder 12, which may be formed, at least in part, by an opening or other feature of the medium 16. Thus, the transducer 14, medium 16 and holder 12 may be formed as a single integrated part, if desired. In some embodiments, the acoustic field may be controlled, the acoustic transducer 14 may be moved, and/or the vessel 3 may be moved (e.g., by way of moving a holder 12, such as a rack, tray, platform, etc., that supports the vessel 3) so that the sample is positioned in a desired location relative to the focal zone 17. In addition, or alternately, the transducer 14 may form the focal zone 17 so that the focal zone 17 is suitably positioned relative to the sample 1 or vessel 4.

To control the acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. The system control circuit 10 may control various other acoustic treatment system 100 functions, such as positioning of the vessel 3 and/or acoustic transducer 14 (a dashed line linking the control circuit 10 to the holder 12 schematically represents an optional positioning system, e.g., including a robot, gantry, screw drive, or other arrangement to move the holder 12), receiving operator input (such as commands for system operation), outputting information (e.g., to a visible display screen, indicator lights, sample treatment status information in electronic data form, and so on), and others.

Figure 8:
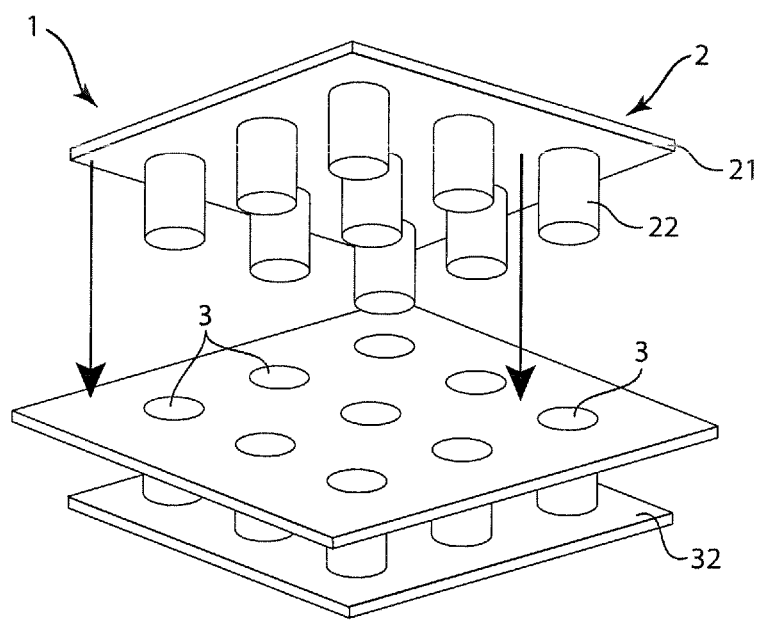
FIG. 8 shows a perspective view of an illustrative embodiment that includes a plurality of vessels.

A sample holder 1 in accordance with aspects of the invention is not limited to holding a single sample in a single vessel. Instead, a sample holder may include two or more vessels 3 and may hold two or more samples. FIG. 8 shows one illustrative embodiment in which a sample holder 1 includes a plurality of vessels 3 that are formed in a single well plate-type format. In one embodiment, the vessels 3 may be molded into a single unitary element that forms the sidewall of each vessel 3, but has an open bottom. A single sheet of flexible film, such as a Kapton film 32, may be arranged to close the bottom opening of the vessels 3, e.g., by adhering the film to the lower end of the vessel sidewalls. This arrangement may provide each of the vessels 3 not only with a flexible film at a lower end of the vessels (e.g., for use in crushing a sample), but also provide each vessel with an acoustic window 32 for admitting acoustic energy into the vessel to treat a sample. The sample holder 1 may also include a cover 21 that includes a plurality of plungers 22 arranged to be inserted into a corresponding vessel 3 so that a sample in each of the vessels 3 may be simultaneously crushed. Each of the plungers 22 may include a seal element 23, such as an o-ring or other arrangement to help isolate a sample from an exterior environment. The plungers 22 may be formed to be solid so that a single plate may press down on the cover 21 to push the plungers 22 into the vessels 3. Alternately, the plungers 22 may be arranged to have a recess in the top surface to receive a corresponding arbor or pin that is inserted into the recess and used to push the plunger into the vessel. This arrangement may allow the plungers to be made less robustly, e.g., to act more as a liner that separates the sample from the received arbor or pin, and allows the arbor to bear most of the mechanical force of crushing. The cover 21 may be made of any suitable material, such as molded of a glass hardened plastic material or other. In one embodiment, the sample holder 1 may be arranged to simultaneously crush a sample 10, such as a corn kernel, in each vessel 3, although arrangements for use with other sample materials are possible.

Figure 9:
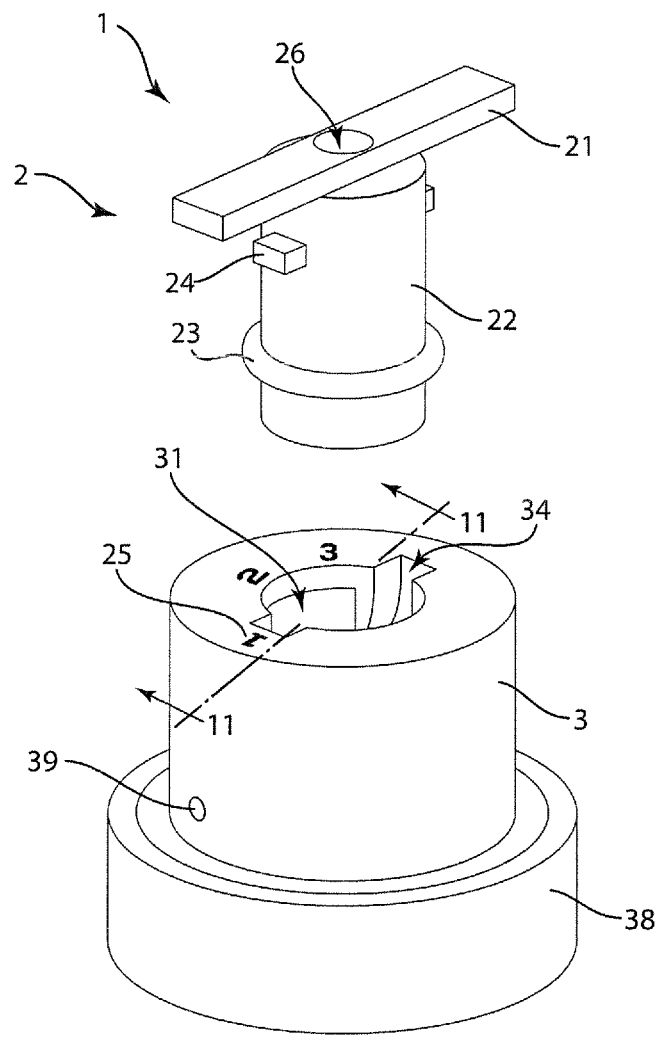
FIG. 9 shows a perspective view of another illustrative embodiment of a sample holder.

FIG. 9 shows a perspective view of another illustrative embodiment of a sample holder 1. Features of the embodiment of FIG. 9 that are similar to those of FIG. 1 are not discussed in detail, but rather only the differences are highlighted. The cap 2 in this embodiment includes a cover 21 in the form of a T-handle on the top of the plunger 22. Similar to the FIG. 1 embodiment, the plunger 22 includes protrusions 24 that interact with surface features 33 of the vessel 3, but in this embodiment, the cap 2 includes a recess 26 arranged to receive an arbor, rod or other component used to push the plunger 22 into the interior space 31 and crush a sample 10. In this embodiment, the vessel includes indicators 25 in for form of members "1," "2," and "3." One end of the T-handle cover 21 indicates the state of the cap 2 by its proximity to a number on the vessel 3, i.e., "1" indicates that the cap 1 is in an open condition, "2" indicates that the cap 2 is in storage condition, and "3" indicates that the cap 2 is in the crush-enabled condition.

A typical way to use the holder 1 of FIG. 8 would be to place a sample in the vessel 3 and insert the plunger 22 into the interior space 31 and put the cap 2 into the storage condition, i.e., turn the cover 21 to the "2" position. The sample could be stored in this condition for any desired amount of time. To crush the sample, the cap 2 can be turned clockwise to the "3" position, and the plunger 22 forced into the interior space 31 e.g., by inserting an arbor into the recess 26 and forcing the plunger 22 downward. After crushing, the cap 2 can be turned counterclockwise to the "1" position, which causes/allows the plunger 22 to be withdrawn from the interior space 31.

Figure 10:
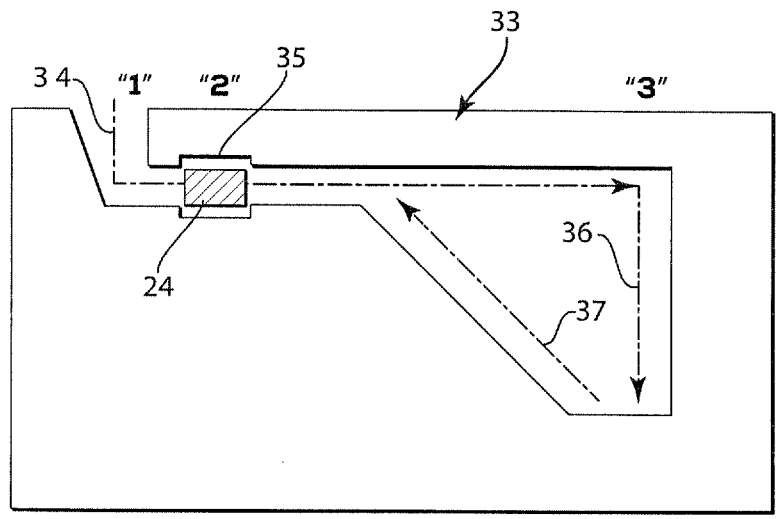
FIG. 10 shows a map of surface features of the internal sidewall of the FIG. 9 vessel.

FIG. 10 shows a map of the surface features 33 in the interior space 31 that extend between the lines 11-11 in FIG. 9. To engage the cap 2 with the vessel 3, the protrusions 24 of the plunger 22 enter a respective entrance slot 34 (the open condition "1") so that the cap 2 can be turned clockwise to position the protrusions 24 at the storage slot 35 (the storage condition "2"). As shown in FIG. 10, the storage slot 35 may include detent features (e.g., upper and lower notches) that may help capture the protrusion 24 at the storage condition.

As will be understood, the storage slot 35 and the size and/or shape of the detent features may be arranged to help capture the protrusion 24, e.g., if there is negative or positive pressure in the interior space 31 relative to an exterior environment. A resilient element (such as a spring or living hinge feature) may additionally be used at the storage slot 35 to help capture the protrusion 24, yet allow release upon application of a suitable rotation force to the cap 2. Further clockwise rotation puts the protrusions 24 into the crush slot 36 (the crush enable condition "3") which allows the plunger to be moved downwardly to crush the sample. After crushing, the protrusions 24 are located at the bottom of the crush slot 36. To withdraw the plunger 22, the cap 2 may be rotated counterclockwise so that the protrusions 24 ride on angled surfaces of an exit slot 37 that help to withdraw the plunger 22 from the interior space 31. The cap 2 may be placed in the storage condition with the protrusions 24 at the storage slot 35, or the cap 2 could be further rotated so the protrusions 24 exit at the entrance slot 34. A portion of the entrance slot 34 (on the left in FIG. 10) may be angled to help withdraw the plunger from the interior space, e.g., counterclockwise rotation of the cap 2 may cause the protrusions 24 to ride up the angled surface of the entrance slot 34 to help withdraw the plunger 22.

Figure 11:
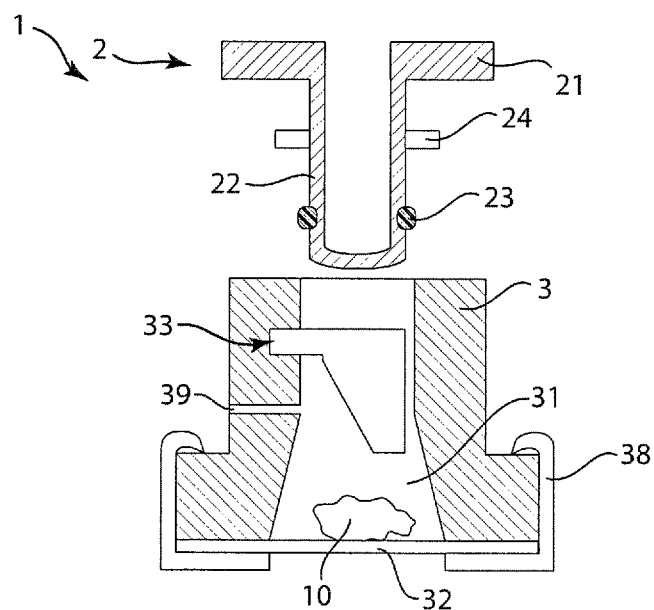
FIG. 11 shows a cross sectional view of the FIG. 9 embodiment along the line 11-11.

FIG. 11 shows a cross sectional view of the holder 1 along the lines 11-11 in FIG. 9. In this embodiment, an acoustic window 32 is attached at the bottom of the vessel 3 by a crimp fitting 38, e.g., a metal cover with a hole to expose the window 32 that wraps around the bottom of the vessel 3 in a way similar to how a metal bottle cap engages a glass bottle top. This arrangement can allow for replacement of the window 32, e.g., a piece of film material, if desired. For example, different samples may require different acoustic windows, or a broken or worn window may be replaced so the vessel can be reused. In this embodiment, the interior sidewall of the vessel 3 flares outwardly near the bottom, which allows the seal element 23 to disengage from the sidewall during crushing. This can help the plunger move in the interior space 31 without restriction during crushing. However, the seal element 23 may engage with the sidewall when in the storage condition to hermetically seal the interior space 31. Also, this embodiment differs from the FIG. 1 embodiment in that the cap 2 includes the recess 26 that extends downwardly into the plunger 22. This arrangement allows an arbor, rod or other element to extend into the plunger 22 for crushing purposes. As mentioned above, this may allow the arbor to bear the crushing force, allowing the plunger to be made less robustly. This embodiment also includes a fluid inlet 39 that allows for the addition of fluid to the interior space 31. For example, the fluid inlet 39 may include a septum arranged to accept a syringe tip so as to inject fluid into the vessel 3. Displaced gas may exit through the inlet 39, or through another port.

Figure 12:
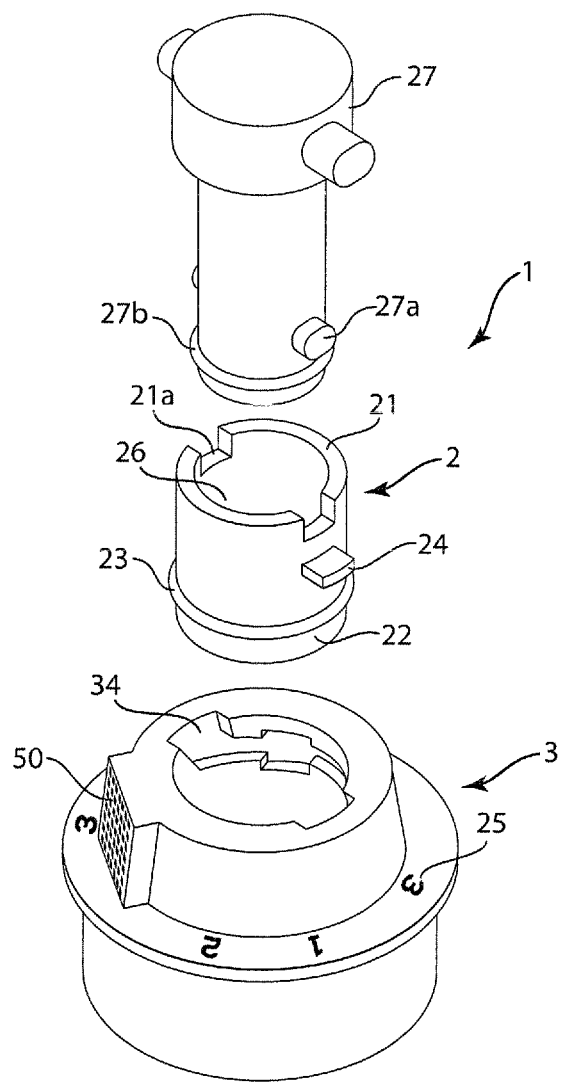
FIG. 12 shows a perspective view of a sample holder having a cap that can be operated by a separable tool.
Figure 13:
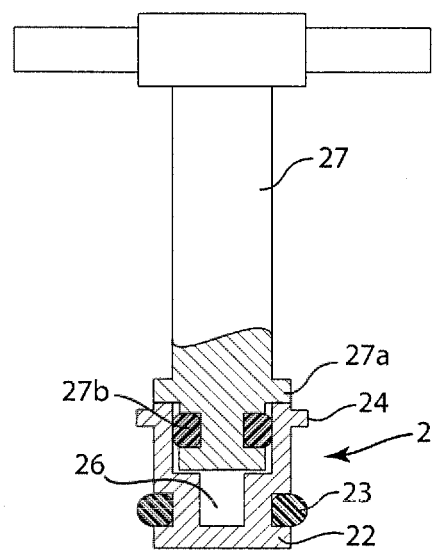
FIG. 13 shows a cross sectional view of a tool and cap of the FIG. 12 embodiment.
Figure 14:
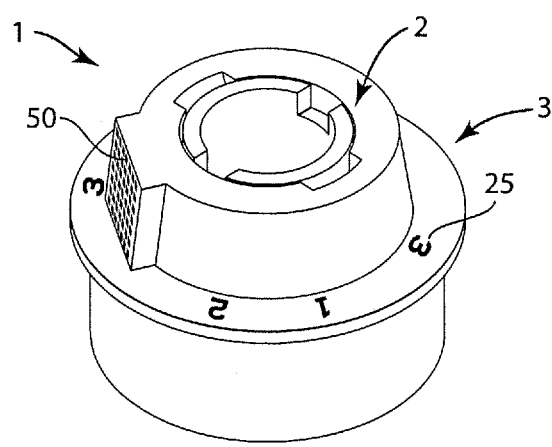
FIG. 14 shows a perspective view of the FIG. 12 embodiment with the cap engaged with the vessel.

In another embodiment shown in FIGS. 12-14, the T-handle portions of the cover 21 may be eliminated, and the cap 2 may be arranged to interact with a tool 27 that can engage with the cap 2, e.g., in a recess 26 or other portion of the cap 2. The tool 27 may function as a key so that the tool 27 can be used to rotate the cap 2 and/or be used to force the cap 2 to crush a sample. The tool 27 may have protrusions 27a, ears, a detent feature or other arrangement to help engage the cap 2 for rotation and/or removal of the cap 2 from the vessel. In this embodiment, protrusions 27a on the tool 27 engage with notches 21a in the cover 21 of the cap 2. This engagement can allow the tool 27 to apply a rotating force to the cap 2. The tool 27 may also include an o-ring or other engagement member 27b to help allow the tool 27 to support the cap 2 vertically. For example, as shown in the cross-sectional view of FIG. 13, the engagement member 27b may frictionally engage with the recess 26 of the cap 2 so that the tool 27 can be used to lift and place the can 2 on the vessel 3, or remove the cap from the vessel 3. Grooves or other features may be provided in the recess 26 to help prevent the creation of a high or low pressure condition in the recess 26 when the tool 27 is engaged or disengaged from the cap 2. With the protrusions 24 of the cap 2 engaged with the vessel 3, e.g., in the storage condition "2," the engagement member 27b may be disengaged from the recess 26 by lifting the tool 27 from the cap 2. FIG. 14 shows the cap 2 engaged with the vessel 3 and the tool 27 removed from the cap 2. The cap 2 may be made with a relatively low profile as shown in FIG. 14, e.g., to help prevent accidental or other unwanted movement of the cap 2 relative to the vessel 3.

In some embodiments, the sample holder may be equipped with an identifier 50, such as a barcode, RFID tag, alphanumeric text, a security or other feature that allows the sample holder 1 to be identified and/or be associated with the samples held in the vessels 3. In one embodiment shown in FIGS. 12 and 14, a bar code 50 may be laser etched or otherwise formed in the vessel 3 and used to keep track of vessel and/or sample identity. The identifier 50 may be used in a variety of different ways, e.g., to track the movement of the sample holder 1, to associate information regarding a sample held by the vessels 3 with the sample holder 1 in a database, and so on. In other embodiments, the identifier may provide information for a processing device, e.g., may provide information to a crushing device to cause crushing of the sample at a desired crushing force, impact energy, impact speed, or other crushing parameter. Alternately, the identifier may provide information to an acoustic treatment device, e.g., to control acoustic treatment parameters such as energy intensity, frequency, duration, etc.

Aspects of the invention also include the use of a sample holder as described above, such as processes of providing a sample in a vessel, engaging a cap with the vessel in a storage condition, placing the cap in a crush-enable condition, crushing the sample using the cap, and removing the cap from the vessel. Other processes are included as well, such as providing a sample in a vessel, crushing the sample using a cap, and acoustically treating the crushed sample while in the vessel, e.g., by transmitting acoustic energy through an acoustic window of the vessel. Another aspect of the invention includes, providing a sample in a vessel, crushing the sample using a cap, positioning the cap to define a specified volume in the vessel, and adding fluid to the vessel to fill the specified volume while the cap covers an opening of the vessel.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only. It will be apparent that other embodiments and various modifications may be made to the present invention without departing from the scope thereof. The foregoing description of the invention is intended merely to be illustrative and not restrictive thereof. The scope of the present invention is defined by the appended claims and equivalents thereto.

The invention claimed is:

1. A sample holder comprising:
   a vessel defining an interior space to hold a sample, the vessel having an opening at an upper side of the vessel through which the interior space is accessible and an acoustic window arranged to admit acoustic energy into the interior space for acoustic treatment of a sample by applying focused acoustic energy to the sample; and
   a cap including a cover and a plunger arranged to engage with the vessel so as to cover the opening, the plunger being arranged for extension into the interior space and movement from a first position to a second position relative to the vessel to provide a force to a sample to crush the sample in the interior space, wherein the cap is arranged to engage with the vessel in a storage condition in which the plunger is prevented from moving to crush a sample in the interior space, and to engage with the vessel in a crush-enabled condition in which the plunger is movable to crush a sample in the interior space.

2. The holder of claim 1, wherein the cap is arranged to maintain a hermetic seal for the interior space in the first position of the plunger.

3. The holder of claim 1, wherein the acoustic window includes an opening in the vessel that is covered by a flexible film.

4. The holder of claim 3, wherein the flexible film has a thickness of between about 0.5 mil and 5 mil.

5. The holder of claim 3, wherein the flexible film includes a polyimide, a polysulfone, a fluorinated polymer or a liquid crystal polymer material.

6. The holder of claim 1, wherein the cap is arranged to engage with the vessel in the storage condition in which the plunger is located at a first depth in the interior space, and the cap is arranged to engage with the vessel in a crush position in which the plunger is located at a second depth in the interior space that is greater that the first depth.

7. The holder of claim 6, wherein the cap is arranged such that, with the plunger at the second depth, rotation of at least a portion of the cap relative to the vessel withdraws the plunger at least partially from the interior space.

8. The holder of claim 6, wherein the plunger is prevented from movement into the interior space with the cap in the storage condition.

9. The holder of claim 1, wherein the cap is rotatable relative to the vessel between the storage and crush-enabled conditions.

10. The holder of claim 1, wherein the plunger includes a seal element that engages with the vessel and seals a portion of the interior space from an exterior environment.

11. The holder of claim 1, wherein the cover and plunger are fixed relative to each other.

12. The holder of claim 1, wherein the vessel and/or the cap include one or more indicators to indicate that the cap is in the storage or crush-enabled condition.

13. The holder of claim 1, wherein the vessel and plunger are arranged to provide a crushing force to a sample material that transfers energy to the sample of at least about 10 Joules.

14. The holder of claim 1, wherein the vessel and cap are arranged to provide a crushing force to a sample that includes one of a seed, bone, rock, stone, sand, glass, metal, tree bark, and/or fragments and combinations thereof.

15. The holder of claim 1, wherein the acoustic window cooperates with the plunger to provide a force to the sample to crush the sample.

16. The holder of claim 15, wherein the acoustic window and the plunger are arranged to provide a force to the sample located between the acoustic window and the plunger.

17. The holder of claim 1, wherein the vessel and cap are arranged to apply a force to the sample at temperatures below about −40 degrees Celsius.

18. A sample holder comprising:
- a vessel defining an interior space to hold a sample, the vessel having a top opening through which the interior space is accessible; and
- a cap including a cover and a plunger arranged to engage with the vessel so as to cover the opening, the plunger being arranged to extend into the interior space for movement from a first position to a second position to provide a force to the sample to crush the sample in the interior space, wherein the cover is arranged to be put in a storage condition in which the plunger is locked in position relative to the vessel to define a specified volume in the interior space.

19. The holder of claim 18, wherein the plunger is arranged to hermetically seal the interior space with the cap in the storage condition.

20. The holder of claim 18, wherein the vessel includes an acoustic window suitable to admit acoustic energy into the interior space for acoustic treatment of a sample in the interior space.

21. The holder of claim 20, wherein the acoustic window includes a polyimide, a polysulfone, a fluorinated polymer or a liquid crystal polymer material.

22. The holder of claim 20, wherein the acoustic window cooperates with the plunger to provide a force to the sample to crush the sample.

23. The holder of claim 21, wherein the vessel and cap are arranged to apply a force to the sample at temperatures below about −40 degrees Celsius.

24. The holder of claim 18, wherein the cap is arranged to engage with the vessel in the storage condition in which the plunger is located at a first depth in the interior space, and the cap is arranged to engage with the vessel in a crush position in which the plunger is located at a second depth in the interior space that is greater that the first depth.

25. The holder of claim 24, wherein cap engages the vessel such that, with the plunger at the second depth, rotation of the cap relative to the vessel withdraws the plunger at least partially from the interior space.

26. The holder of claim 24, wherein the plunger is prevented from movement into the interior space with the cap in the storage condition.

27. The holder of claim 18, wherein the cap is arranged to engage with the vessel in the storage condition in which the plunger is prevented from moving to crush a sample in the interior space, and to engage with the vessel in a crush-enabled condition in which the plunger is movable to crush a sample in the interior space.

28. The holder of claim 27, wherein the cap is rotatable relative to the vessel between the storage and crush-enabled conditions.

29. The holder of claim 27, wherein the vessel and/or the cap include one or more indicators to indicate that the cap is in the storage or crush-enabled condition.

30. The holder of claim 18, wherein the plunger includes a seal element that engages with the vessel and seals a portion of the interior space in which a sample is placeable from an exterior environment.

31. The holder of claim 18, wherein the vessel includes an inlet through which a liquid can be provided to the interior space while the cover is in the storage condition.

32. The holder of claim 31, wherein the inlet includes a septum arranged to permit both inflow of liquid and outflow of fluid.

33. The holder of claim 18, wherein the vessel and plunger are arranged to provide a crushing force to a sample material that transfers energy to the sample of at least about 10 Joules.

34. The holder of claim 18, wherein the specified volume is between about 10 microliters to about 1 milliliter.

35. The holder of claim 18, wherein the flexible film and plunger are arranged to transmit a crushing force to the sample at temperatures less than about −40 degrees C. without cracking, tearing, or ripping when exposed to the crushing force.

36. The holder of claim 18, wherein the vessel and cap are arranged to provide a crushing force to a sample that includes one of a seed, bone, rock, stone, sand, glass, metal, tree bark, and/or fragments and combinations thereof.

37. A sample holder comprising:
- a vessel defining an interior space to hold a sample, the vessel having an opening at an upper side of the vessel through which the interior space is accessible; and
- a cap including a cover and a plunger arranged to engage with the vessel so as to cover the opening and seal the interior space closed, the plunger being arranged for extension into the interior space and movement from a first position to a second position relative to the vessel to provide a force to a sample to crush the sample in the interior space,
- wherein the cap is arranged to be put in a storage condition in which the plunger is prevented from movement to the second position, and to be put in a crush-enable condition in which the plunger is released for sliding movement from the first position to the second position.

38. The holder of claim 37, wherein the cap is rotated relative to the vessel between the storage condition and the crush-enable condition.

39. The holder of claim 37, wherein the cap and vessel are configured such that, with the plunger in the second position, rotation of the cap relative to the vessel moves the plunger from the second position toward the first position.

40. The holder of claim 37, wherein rotation of the cap relative to the vessel with the plunger at the second position at least partially withdraws the plunger from the interior space.

41. The holder of claim 37, wherein the cap includes at least one protrusion that engages with a corresponding slot in the vessel to put the cap in the storage condition.

42. The holder of claim 37, wherein the cap includes at least one protrusion that engages with a ramp of the vessel with the plunger at the second position such that rotation of the cap relative to the vessel causes the at least one protrusion to move along the ramp to at least partially withdraw the plunger from the interior space.

43. A sample holder comprising:
- a vessel defining an interior space to hold a sample, the vessel having a top opening through which the interior space is accessible; and
- a cap including a cover and a plunger arranged to engage with the vessel so as to cover the opening and to seal the interior space closed, the plunger being arranged to extend into the interior space for movement from a first position to a second position to provide a force to the sample to crush the sample in the interior space,
- wherein the vessel or cap includes a fluid inlet arranged to admit fluid into the interior space with the cap providing a hermetic seal for the interior space, and wherein the cover is arranged to be put in a storage condition in which the plunger is locked in position relative to the vessel to define a specified volume in the interior space.

44. The holder of claim 43, wherein the inlet includes a septum arranged to permit both inflow of liquid and outflow of fluid.

45. The holder of claim 43, wherein the plunger is arranged to hermetically seal the interior space with the cap in the storage condition.

46. A sample holder comprising:
   a vessel defining an interior space to hold a sample, the vessel having an opening at an upper side of the vessel through which the interior space is accessible and an acoustic window arranged to admit acoustic energy into the interior space for acoustic treatment of a sample by applying focused acoustic energy to the sample; and
   a cap including a cover and a plunger arranged to engage with the vessel so as to cover the opening, the plunger being arranged for extension into the interior space and movement from a first position to a second position relative to the vessel to provide a force to the sample to crush the sample in the interior space, wherein the cap is arranged to engage with the vessel in a storage condition in which the plunger is located at a first depth in the interior space, and the cap is arranged to engage with the vessel in a crush position in which the plunger is located at a second depth in the interior space that is greater that the first depth, and wherein the cap is arranged such that, with the plunger at the second depth, rotation of at least a portion of the cap relative to the vessel withdraws the plunger at least partially from the interior space.

47. The holder of claim 46, wherein the cap is arranged to maintain a hermetic seal for the interior space in the first position of the plunger.

48. The holder of claim 46, wherein the acoustic window includes an opening in the vessel that is covered by a flexible film.

49. The holder of claim 46, wherein the plunger is prevented from movement into the interior space with the cap in the storage condition.

50. The holder of claim 46, wherein the cap is arranged to engage with the vessel in a storage condition in which the plunger is prevented from moving to crush the sample in the interior space, and to engage with the vessel in a crush-enabled condition in which the plunger is movable to crush the sample in the interior space.

51. The holder of claim 50, wherein the cap is rotatable relative to the vessel between the storage and crush-enabled conditions.

52. The holder of claim 46, wherein the plunger includes a seal element that engages with the vessel and seals a portion of the interior space from an exterior environment.

* * * * *